(12) United States Patent
Muschler et al.

(10) Patent No.: US 9,045,735 B2
(45) Date of Patent: Jun. 2, 2015

(54) ENRICHMENT OF TISSUE-DERIVED ADULT STEM CELLS BASED ON RETAINED EXTRACELLULAR MATRIX MATERIAL

(75) Inventors: George Muschler, Cleveland Heights, OH (US); Tonya Caralla, Lakewood, OH (US); Vincent Hascall, Cleveland Heights, OH (US); Ronald Midura, Shaker Heights, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 799 days.

(21) Appl. No.: 12/594,493

(22) PCT Filed: Apr. 3, 2008

(86) PCT No.: PCT/US2008/059256
§ 371 (c)(1),
(2), (4) Date: Mar. 1, 2010

(87) PCT Pub. No.: WO2008/124494
PCT Pub. Date: Oct. 16, 2008

(65) Prior Publication Data
US 2010/0167316 A1 Jul. 1, 2010

Related U.S. Application Data

(60) Provisional application No. 60/921,517, filed on Apr. 3, 2007.

(51) Int. Cl.
| C12N 5/02 | (2006.01) |
| C12N 5/071 | (2010.01) |
| C12N 5/00 | (2006.01) |
| C12N 5/0775 | (2010.01) |

(52) U.S. Cl.
CPC .......... *C12N 5/0663* (2013.01); *C12N 2500/38* (2013.01); *C12N 2501/39* (2013.01); *C12N 2501/905* (2013.01); *C12N 2533/80* (2013.01)

(58) Field of Classification Search
CPC ............. C12N 5/0663; C12N 2500/38; C12N 2501/39; C12N 2501/905
USPC .......................... 435/375, 366, 380, 395, 402
See application file for complete search history.

(56) References Cited

U.S. PATENT DOCUMENTS

| 4,608,199 A | 8/1986 | Caplan et al. |
| 4,609,551 A | 9/1986 | Caplan et al. |
| 5,197,985 A | 3/1993 | Caplan et al. |
| 5,226,914 A | 7/1993 | Caplan et al. |
| 5,425,580 A | 6/1995 | Beller |
| 5,433,330 A | 7/1995 | Yatsko et al. |
| 5,486,359 A | 1/1996 | Caplan et al. |
| 5,569,308 A | 10/1996 | Sottosanti |
| 5,626,861 A | 5/1997 | Laurencin et al. |
| 5,634,879 A | 6/1997 | Mueller-Glauser et al. |
| 5,645,729 A | 7/1997 | Priegnitz et al. |
| 5,700,289 A | 12/1997 | Breitbart et al. |
| 5,718,899 A | 2/1998 | Gristina et al. |
| 5,733,542 A | 3/1998 | Haynesworth et al. |
| 5,766,618 A | 6/1998 | Laurencin et al. |
| 5,824,084 A | 10/1998 | Muschler |
| 5,914,121 A | 6/1999 | Robey et al. |
| 6,037,519 A | 3/2000 | McKay |
| 6,045,555 A | 4/2000 | Smith et al. |
| 6,049,026 A | 4/2000 | Muschler |
| 6,142,998 A | 11/2000 | Smith et al. |
| 6,723,131 B2 | 4/2004 | Muschler |
| 7,465,766 B2 | 12/2008 | Calabro et al. |
| 8,568,761 B2 * | 10/2013 | Matheny ...................... 424/423 |
| 2004/0033218 A1 | 2/2004 | Yacoby-Zeevi |
| 2007/0036768 A1 | 2/2007 | Fraser et al. |
| 2008/0033548 A1 | 2/2008 | Xuenong et al. |

FOREIGN PATENT DOCUMENTS

| CN | 1287166 | * | 3/2001 |
| CN | 1287166 A | | 3/2001 |
| DE | 3810803 A1 | | 10/1989 |
| EP | 0742020 A2 | | 11/1996 |
| JP | 03-158164 | | 7/1991 |
| JP | 06-086809 | | 3/1994 |
| JP | 06-142185 | | 5/1994 |
| JP | 08-112341 | | 5/1996 |

(Continued)

OTHER PUBLICATIONS

Ngo, in the Protein Folding Problem and Tertiary Structure Prediction, Merz et al. (eds.), Birkhauser Boston: Boston, MA, pp. 433 and 492-495, 1994.*

(Continued)

*Primary Examiner* — Maria Leavitt
(74) *Attorney, Agent, or Firm* — Pearne & Gordon LLP

(57) ABSTRACT

Methods for enriching, detecting, or using adult stem cells through the use of recognition ligands that specifically bind to ECM components retained to the surfaces of adult stem cells are described. An ECM component such as hyaluronan that is retained to the surfaces of adult stem cells when removed from animal tissues can be used to detect a diverse population of adult stem cells based on the nature of the ECM niche region in which the adult stem cells normally reside. For example, a separation method such as magnetic separation can be used to detect and isolate or enrich adult stem cells based on a recognition ligand that is specific for an ECM component that is retained to the surfaces of adult stem cells to a greater degree than to other cells in the population.

6 Claims, 1 Drawing Sheet

(56) References Cited

FOREIGN PATENT DOCUMENTS

| JP | 2006-345728 | * 12/2006 |
| WO | 96/01641 | 1/1996 |
| WO | 97/40137 | 10/1997 |
| WO | 00/49319 | 8/2000 |

OTHER PUBLICATIONS

Voet, Biochemistry John Wiley and Sons, 1990, pp. 126-128.*
Fibronectin From Wikipedia, the free encyclopedia pp. 3-10.*
Varki, A. et al., eds., Essentials of Glycobiology, Cold Spring Harbor Laboratory Press, New York, 1999.
Avigdor, A. et al., "CD44 and hyaluronic acid cooperate with SDF-1 in the trafficking of human CD34+ stem/ progenitor cells to bone marrow," Blood 103, pp. 2981-2989, 2004.
Boiret, N. et al., "CD34+CDw90(Thy-1) + subset colocated with mesenchymal progenitors in human normal bone marrow hematon units is enriched in colony-forming unit megakaryocytes and long-term culture-initiating cells," Exp. Hematology 31, pp. 1275-1283, 2003.
Boiret, N. et al., "Characterization of nonexpanded mesenchymal progenitor cells from normal adult human bone marrow," Exp. Hematology 33, pp. 219-225, 2005.
Bruder, S.P. et al, "Monoclonal antibodies reactive with human osteogenic cell surface antigens," Bone 21(3), pp. 225-235, Sep. 1997.
Campioni, D. et al., "Functional and immunophenotypic characteristics of isolated CD105+ and fibroblast+ stromal cells from AML: implications for their plasticity along endothelial lineage," Cytotherapy 5(1), pp. 66-79, 2003.
Clark, J.M., Jr. et al., Experimental Biochemistry, 2nd Edition, pp. 16 and 243, 1977.
Day, A.J. et al., "Hyaluronan-binding proteins: Tying up the giant," J. Biol. Chem. 277(7), pp. 4585-4588, Feb. 15, 2002.
Deschaseaux, F. et al., "Direct selection of human bone marrow mesenchymal stem cells using an anti-CD49a antibody reveals their CD45med,low phenotype," Br. J. Haematology 122, pp. 506-517, 2003.
Fleming, J.E. et al., "Monoclonal antibody against adult marrow-derived mesenchymal stem cells recognizes developing vasculature in embryonic human skin," Dev. Dyn. 212, pp. 119-132, 1998.
Goshima, J. et al., "The origin of bone formed in composite grafts of porous calcium phosphate ceramic loaded with marrow cells," Clin. Orthopaedics Related Res. 269, pp. 274-283, 1991.
Gronthos, S. et al., "Integrin-mediated interactions between human bone marrow stromal precursor cells and the extracellular matrix," Bone 28(2), pp. 174-181, Feb. 2001.
Gronthos, S., et al., "Molecular and cellular characterisation of highly purified stromal stem cells derived from human bone marrow," J. Cell Sci. 116(9), pp. 1827-1835, 2003.
Haynesworth, S.E. et al., "Cell surface antigens on human marrow-derived mesenchymal cells are detected by monoclonal antibodies," Bone 13, pp. 69-80, 1992.
Hernigou, P. et al., "Percutaneous autologous bone-marrow grafting for nonunions: Influence of the number and concentration of progenitor cells," J. Bone Joint Surg. 87-A, pp. 1430-1437, 2005.
Jankowski, R.J. et al., "Flow cytometric characterization of myogenic cell populations obtained via the preplate technique: Potential for rapid isolation of muscle-derived stem cells," Human Gene Therapy 12(6), pp. 619-628, Apr. 10, 2001.
Jing, Y. et al., "Blood progenitor cell separation from clinical leukapheresis product by magnetic nanoparticle binding and magnetophoresis," Biotechnol. Bioeng. 96(6), pp. 1139-1154, Apr. 15, 2007.
Jing, Y. et al., "Negative selection of hematopoietic progenitor cells by continuous magnetophoresis," Exp. Hematology 35, pp. 662-672, 2007.
Jones, E.A. et al, "Isolation and characterization of bone marrow multipotential mesenchymal progenitor cells," Arthritis & Rheumatism 46(12), pp. 3349-3360, Dec. 2002.

Jones, E.A. et al., "Optimization of a flow cytometry-based protocol for detection and phenotypic characterization of multipotent mesenchymal stromal cells from human bone marrow," Cytometry Part B (Clinical Cytometry) 70B, pp. 391-399, 2006.
Klees, R.F. et al., "Laminin-5 induces osteogenic gene expression in human mesenchymal stem cells through an ERK-dependent pathway," Molecular Biology of the Cell 16, pp. 881-890, Feb. 2005.
Knudson, C.B. et al., "Hyaluronan-binding proteins in development, tissue homeostasis, and disease," FASEB J. 7, pp. 1233-1231, Oct. 1993.
Kolf, C.M et al., "Biology of adult mesenchymal stem cells: regulation of niche, self-renewal and differentiation," Arthritis Res. & Therapy 9, p. 204, 10 pages, 2007.
Lang, P. et al., "Transplantation of highly purified CD34+ progenitor cells from unrelated donors in pediatric leukemia," Blood 101(4), pp. 1630-1636, Feb. 15, 2003.
Lisignoli, G. et al., "Hyaluronan-based polymer scaffold modulates the expression of inflammatory and degradative factors in mesenchymal stem cells: involvement of Cd44 and Cd54," J. Cell. Physiol. 207, pp. 364-373, 2006.
Majors, A.K. et al., "Characterization of human bone marrow stromal cells with respect to osteoblastic differentiation," J. Orthopaedic Res. 15, pp. 546-557, 1997.
Majumdar, M.K. et al., "Isolation, characterization, and chondrogenic potential of human bone marrow-derived multipotential stromal cells," J. Cell. Physiol. 185, pp. 98-106, 2000.
Mehlhorn, A.T. et al., "Differential expression pattern of extracellular matrix molecules during chondrogenesis of mesenchymal stem cells from bone marrow and adipose tissue," Tissue Engineering 12(10), pp. 2853-2863, 2006.
Midura, R.J. et al. "Parathyroid hormone rapidly stimulates hyaluronan synthesis by periosteal osteoblasts in the tibial diaphysis of the growing rat," J. Biol. Chem. 278(51), pp. 51462-51468, Dec. 19, 2003.
Moore, L.R. et al., "Control of magnetophoretic mobility by susceptibility-modified solutions as evalutated by cell tracking velocimetry and continuous magnetic sorting," Anal. Chem. 76(14), pp. 8899-3907, Jul. 15, 2004.
Muschler, G.F. et al., "Aspiration to obtain osteoblast progenitor cells from human bone marrow: the influence of aspiration volume," J. Bone Joint Surgery [Am.] 79-A(11), pp. 1699-1709, Nov. 1997.
Muschler, G.F. et al., "Age- and gender-related changes in the cellularity of human bone marrow and the prevalence of osteoblastic progenitors," J. Orthopaedic Res. 19, pp. 117-125, 2001.
Muschler, G.F. et al., "Spine fusion using cell matrix composites enriched in bone marrow-derived cells," Clin. Orthopaedics and Related Res. 407, pp. 102-118, Feb. 2003.
Muschler, G.F. et al., "Practical modeling concepts for connective tissue stem cell and progenitor compartment kinetics," J. Biomed. and Biotech. 2003(3), pp. 170-193, 2003.
Muschler, G.F. et al., "Engineering principles of clinical cell-based tissue engineering," J. Bone Joint Surgery [Am.] 86-A(7), pp. 1541-1558, Jul. 2004.
Muschler, G.F. et al., "Selective retention of bone marrow-derived cells to enhance spinal fusion," Clin. Orthop. Related Res. 432, pp. 242-251, Mar. 2005.
Mustoe, T.A. et al., "Growth factor-induced acceleration of tissue repair through direct and inductive activities in a rabbit dermal ulcer model," J. Clin. Invest. 87, pp. 694-703, Feb. 1991.
Quirici, N. et al., "Isolation of bone marrow mesenchymal stem cells by anti-nerve growth factor reception antibodies," Exp. Hematology 30, pp. 783-791, 2002.
Reyes, M. et al., "Purification and ex vivo expansion of postnatal human marrow mesodermal progenitor cells," Blood 98(9), pp. 2615-2625, Nov. 1, 2001.
Salasznyk, R.M. et al., "Adhesion to vitronectin and collagen I promotes osteogenic differentiation of human mesenchymal stem cells," J. Biomed. Biotech. 2004(1), pp. 24-34, 2004.
Scadden, D.T., "The stem-cell niche as an entity of action," Nature 441, pp. 1075-1079, Jun. 29, 2006.
Schade, U.M. et al., "Hyaluronate and its receptors in bone marrow," Acta histochemica 108, pp. 141-147, 2006.

(56) References Cited

OTHER PUBLICATIONS

Shi, S. et al., "Perivascular niche of postnatal mesenchymal stem cells in human bone marrow and dental pulp," J. Bone and Mineral Res. 18(4), pp. 696-704, 2003.
Simmons, P.J. et al., "Identification of stromal cell precursors in human bone marrow by a novel monoclonal antibody, STRO-1," Blood 78(1), pp. 55-62, Jul. 1, 1991.
Stemcell Technologies, EasySep® Product Information Sheet, Version 4.1.1, Catalog #18553, #18556 and #18559, Oct. 2007.
Stewart, K. et al, "STRO-1, HOP-26 (CD63), CD49a and SB-10 (CD166) as markers of primitive human marrow stromal cells and their more differentiated progeny: a comparative investigation in vitro," Cell Tissue Res. 313, pp. 281-290, 2003.
Sundström, G. et al., "Localisation and distribution of hyaluronan in normal bone marrow matrix: a novel method to evaluate impending fibrosis?," Eur. J. Haematology 68, pp. 194-202, 2002.
Tondreau, T. et al., "Isolation of BM mesenchymal stem cells by plastic adhesion or negative selection: phenotype, proliferation kinetics and differentiation potential," Cytotherapy 6(4), pp. 372-379, 2004.
Zborowski, M. et al., "Separations based on magnetophoretic mobility," Separation Sci. Tech. 37(16), pp. 3611-3633, 2002.
International Search Report and Written Opinion issued Jun. 25, 2008 in related PCT application PCT/US2008/059256.
Cichy, J. and Pure, E., "The liberation of CD44," The Journal of Cell Biology, Jun. 9, 2003, vol. 161, No. 5, pp. 839-843.
Fraser, J.R. et al., "Hyaluronan: its nature, distribution, functions and turnover," Journal of Internal Medicine, Jul. 1997, vol. 242, No. 1, pp. 27-33, Abstract Only.
Hascall, V.C. et al., "The dynamic metabolism of hyaluronan regulates the cytosolic concentration of UDP-GlcNAc," Matrix Biology, 2014, vol. 35, pp. 14-17.
Karvinen, S. et al., "Keratinocyte Growth Factor Stimulates Migration and Hyaluronan Synthesis in the Epidermis by Activation of Keratinocyte Hyaluronan Synthases 2 and 3," The Journal of Biological Chemistry, Sep. 23, 2003, vol. 278, No. 49, pp. 49495-49504.
Krupa, J.C. et al., "Quantitative continuous assay for hyaluronan synthase," Analytical Biochemistry, Feb. 15, 2007, vol. 361, No. 2, pp. 218-225, obtained via PubMedCentral and provided as pp. 1-21.
Miyake, K. et al., "Hyaluronate Can Function as a Cell Adhesion Molecule and CD44 Participates in Hyaluronate Recognition," The Journal of Experimental Medicine, Jul. 1990, vol. 172, pp. 69-75.
Monslow, J. et al., "Sp1 and Sp3 Mediate constitutive Transcription of the Human Hyaluronan Synthase 2 Gene," The Journal of Biological Chemistry, Jun. 30, 2006, vol. 281, No. 26, pp. 18043-18050.
Nishida, Y. et al., "Antisense Inhibition of Hyaluronan Synthase-2 in Human Articular Chondrocytes Inhibits Proteogycan Retention and Matrix Assembly," The Journal of Biological Chemistry, 1999, vol. 274, No. 31, pp. 21893-21899.
Pienimaki, JP. et al., "Epidermal Growth Factor Activates Hyaluronan Synthase 2 in Epidermal Keratinocytes and Increases Pericellular and Intracellular Hyaluronan," The Journal of Biological Chemistry, Jun. 8, 2001, vol. 276, No. 23, pp. 20428-20435.
Saavalainen, K. et al., "Integration of the Activation of the Human Hyaluronan Synthase 2 Gene Promoter by Common Cofactors of the Transcription Factors Retinoic Acid Receptor and Nuclear Factor kB," The Journal of Biological Chemistry, Apr. 13, 2007, vol. 282, No. 15, pp. 11530-11539.
Tammi, R. et al., "Hyaluronan Synthase Induction and Hyaluronan Accumulation in Mouse Epidermis Following Skin Injury," The Journal of Investigative Dermatology, May 5, 2005, vol. 124, 898-905.
Underhill, C., "CD44: The hyaluronan receptor," 1992, Journal of Cell Science, vol. 103, pp. 293-298.
Vigetti, D. et al., "Metabolic control of hyaluronan synthases," Matrix Biology, 2014, vol. 35, pp. 8-13.
Coulson-Thomas, V.J. et al., "Umbilical Cord Mesenchymal Stem Cells Suppress Host Rejection: The Role of Glycocalyx," The Journal of Biological Chemistry, Aug. 22, 2014, vol. 289, No. 34, pp. 23465-23481.

* cited by examiner

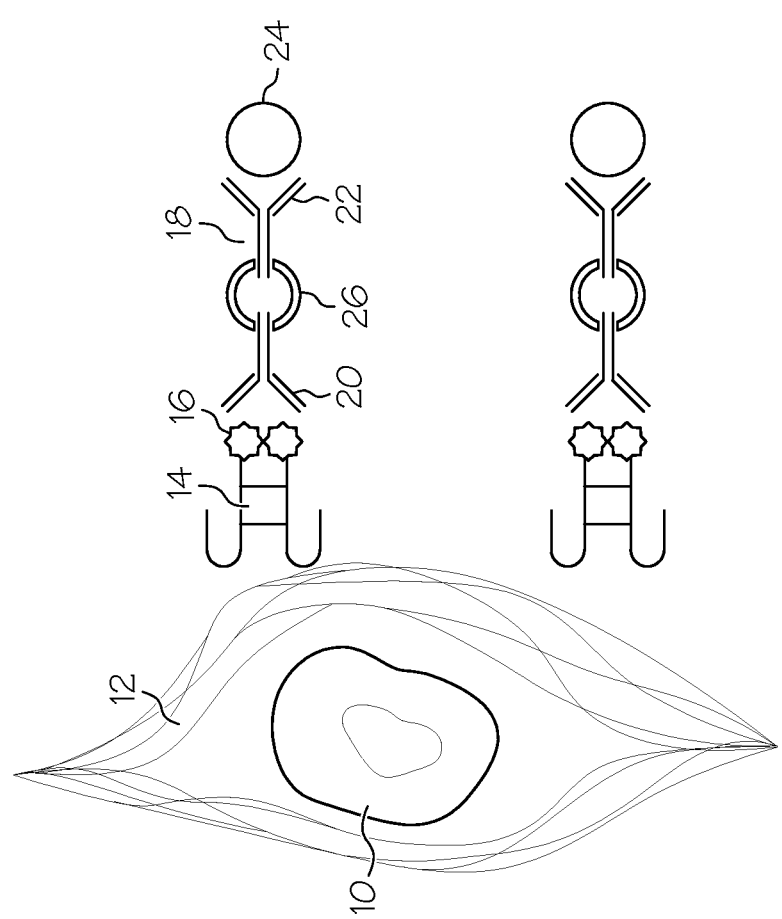

ENRICHMENT OF TISSUE-DERIVED ADULT STEM CELLS BASED ON RETAINED EXTRACELLULAR MATRIX MATERIAL

CONTINUING APPLICATION DATA

This application claims the benefit of U.S. Provisional Application Ser. No. 60/921,517, filed Apr. 3, 2007, which is incorporated by reference herein.

STATEMENT OF GOVERNMENT-SPONSORED RESEARCH

This invention was made with government support under contract No. RO1AR42998 awarded by the National Institutes of Health. The government has certain rights in this invention.

BACKGROUND

Essentially all developing and adult tissues contain one or more populations of stem cells and/or progenitor cells (progenitors) that play a role in the continued maintenance of health of the tissue through remodeling activity. Such stem cell and progenitor populations also contribute to new tissue formation in the event of injury, and represent an essential resource in tissue engineering strategies seeking to repair, augment, replace or regenerate tissues that may be lost due to injury, disease, or degenerative or aging processes.

For example, bone repair requires osteogenic connective tissue progenitors (CTP-Os). In settings where the local population CTP-Os is sufficient, they may be effectively "targeted" using scaffolds or factors, such as bone morphogenic proteins to summon the CTP-Os to where they are needed. However, in settings where the levels of local CTP-Os are suboptimal, optimizing the bone healing response requires transplantation of CTP-Os from an alternative source. Many preclinical studies demonstrate improved graft performance when CTP-Os are added, even to small graft sites in young healthy animals, supporting the premise that the CTP-O population is suboptimal in virtually all clinical settings and that optimal performance from any osteoconductive or osteoinductive material may require augmentation with local CTP-Os.

As a result of the potential importance of progenitor cell populations in maintaining or defining the current health of tissue, and as a resource for cell therapy strategies, methods for the harvest, isolation, assay, characterization, processing and transplantation of progenitor cells have exceptional value, and are expected to be the focus of many advances in health care diagnosis and treatment modalities.

Data available to date from many organ systems has demonstrated that the concentration and prevalence of progenitor cells is generally very low, and varies widely from tissue to tissue and individual to individual. Investigators have speculated that the concentration and prevalence of progenitors are a reflection of the current state of health of a tissue and may also predict the future health of a tissue or individual. As a result, they are likely to have important implications in diagnosis and prediction of disease as well as in the treatment of disease.

Adult stem cells present in native tissues tend to be distinctly different from the much more numerous population of mature cells in native tissue with respect to both morphological as well as chemical and biological properties. Each of these has been used in reported methods for progenitor cell isolation. Cell size, cell density, and granularity have been used as means of enrichment using density separation and countercurrent elutriation. Membrane bound surface markers in the form of membrane bound protein antigens that are uniquely presented on selected stem cell and progenitor populations can be targeted using antibodies. For example, the presence or absence of CD34, c-kit, Sca1 and other markers, alone or in combination, have been used to isolate and fractionate hematopoietic stem cells from marrow and other tissues using fluorescent activated cell sorting (FACS), magnetic separation or affinity columns. adult stem cells also tend to express novel markers and patterns of gene expression. Underlying gene expression, while generally silent, can and has been converted through viral transfection vectors into fluorescent reporters that can be used as a basis for isolation. Finally, cell function, such as the presence of a selective ABC membrane pumps have been identified as a unique feature of several stem cell populations, and have been used to isolate what has been referred to as "side population" cells or SP cells, from marrow and other tissues.

Many markers have been proposed for positive selection of human osteogenic connective tissue progenitors, such as STRO-1, STRO-1 with VCAM-1, and CD antigens 9, 10, 13, 18, 29, 44, 49a, 54, 90, 105, 146 and 166. See Simmons et al., Blood (1991) 78(1), p. 55-62. Alkaline phosphatase and osteocalcin are also markers of some circulating CTP-Os. However, most of these markers are also present on other cell populations, limiting their usefulness for positive selection of CTP-Os. While positive markers have been elusive, CTP-Os may also be differentiated from the vast majority of marrow cells based on markers that they do not express. For example, CTP-Os are negative/dim for CD45 and many other hematopoietic markers. Hematopoietic markers therefore provide possible tools for CTP-O enrichment by negative selection or depletion of non-osteogenic cells.

The most common method of isolation of stem cell and progenitor populations exploits the biological capacity of these cells to proliferate, and particularly the capacity of adult stem cells to proliferate under some conditions in a manner that exponentially increases their number while at the same time preserving one or more desirable biological capacities (e.g. the ability to repopulate bone marrow in an animal that has been depleted of hematopoietic stem cells, or the ability to form new bone tissue in vivo). This strategy of in vitro expansion and purification has been used to prepare populations of cells defined variably as bone marrow stromal cells (MSCs), mesenchymal stem cells (also "MSCs"), mesenchymal progenitor cells (MPCs), multipotent adult progenitor cells (MAPCs), tissue regenerating cells (TRCs), muscle-derived progenitor cells (MDPCs), adipose-derived stem cells (ADSC), and others.

It has long been recognized that while culture-expanded stem cell populations can be prepared that retain desirable biological capabilities, these populations differ significantly from the population of adult stem cells that are present in native tissue from which they are derived. Differences may be expressed in cell size, cell cycle state, expression of markers, and gene expression, as well as intrinsic biological behavior such as responses to growth factors. Furthermore, the use of culture-expanded cells is associated with the need for delay between the harvest of founding cell population and the ultimate use of the resulting expanded cell population. This delay adds significantly to the cost and also to the inconvenience of using culture-expanded cells, because the patient must be exposed to separate procedures; first to collect founding cells, and second to implant cells after in vitro expansion. In addition, in vitro expansion adds the potentially significant risks of bacterial or viral contamination of cells while in vitro, in vitro selection of cells with undetected undesirable biological properties (e.g. tumor forming cells) and even contamination with other cells or mislabeling with respect to the donor of origin.

The rapid isolation and processing of adult stem cells isolated from tissues of an individual at the time of a single therapeutic procedure has great potential value, and avoids many of the drawbacks of culture expanded cell populations cited above. However, rapid processing of freshly isolated cells has itself a number of drawbacks. First, adult stem cells are typically very few in number. The prevalence of progenitor cells (tissue forming cells) within a given tissue can be as high as one in 100 cells, but also as low as one in 1,000,000 cells (or less). Second, stem cells and progenitor populations in native tissues are generally very heterogeneous, in contrast to the relatively homogenous culture-expanded stem cell and progenitor cell populations. No one feature or combination of features can define all adult stem cells in a given tissue. In fact, one must expect that a given tissue will provide a diverse population of adult stem cells that represent cells from multiple stem cell niches within the tissue, each representing a different compartment or niche for the tissue forming cell populations within that tissue. See Muschler et al., J. Biomed. Biotechnol. (2003); 2003(3), p. 170-193.

Rapid processing has two important advantages, however. First, processing strategies can be designed to take advantage of characteristics of freshly isolated cells that may not be preserved when cells are expanded in vitro. Second, due to the high potential that adult stem cells have for proliferation, transplantation of a relatively small number of adult stem cells into a wound in an environment in which cells are likely to survive can result in important and clinically significant improvement in biological outcome. In fact, removal of competing and non-tissue forming cells may be just as important, if not more important, to the performance of transplanted progenitor cells as transplanting them in large numbers. For example, several recent reports have shown that as little as a 3-4 fold increase in the concentration of osteogenic connective tissue progenitor cells can result in significant improvement in bone formation and in union rate in settings of spinal fusion and in settings of bone grafting in long bone defects. See U.S. Pat. Nos. 6,049,026 and 6,723,131, issued to Muschler. Removal of competing cells may eliminate a source of growth factor or signaling molecules that are maladaptive to proliferation and new tissue formation, such as inflammatory cytokines that may stimulate apoptosis (cell death). Removal of competing non-tissue forming cells may also dramatically improve the likelihood that transplanted progenitor cells will survive following transplantation, by reducing local consumption of oxygen and other nutrients. See Muschler et al., J. Bone Joint Surg. Am. (2004) July; 86-A(7), p. 1541-58.

Bone and marrow tissue, including bone marrow harvested using the minimally invasive method of aspiration contains a heterogeneous population of cells, including adult stem cells capable of regenerating connective tissues, blood cells, blood vessels, bone, cartilage, fat, marrow stroma, muscle, tendons, ligaments and other fibrous tissue. These populations include multipotent cells which are individually capable of giving rise to progeny along all three germ lines (i.e. ectoderm, endoderm and mesoderm), pleuripotent progenitors capable of giving rise to progeny that may contribute to multiple mature cell types (e.g. bone, cartilage, fat), and mono- or uni-potent progenitors that are committed to progeny of only one lineage. These diverse and versatile cell sets are used extensively in research settings as well as clinically in bone grafting and tissue engineering endeavors. Bone marrow aspirations offer many advantages as a cell source. In particular, they result in very low morbidity to the patient and provide cells in single cell suspension that can be manipulated and processed using only an anticoagulant, without the need for enzymatic digestion that may modify the cell surface.

One method to increase the concentration of bone forming progenitors is density separation, which is available through use or modification of devices designed for clinical preparation of platelet rich plasma. See Hernigou et al., J. Bone Joint Surg. Am. (2005) July; 87(7), p. 1430-1437. Density separation can increase the CTP concentration 4-8 fold, but is relatively non-selective, and does not change osteogenic CTP prevalence.

Focusing on bone forming progenitors in bone marrow, and using the "gold standard" method for assay of progenitor populations (i.e., the colony forming unit (CFU) assay), investigators have found wide variation between individuals and between individual aspirate samples, but a mean prevalence of osteogenic CTPs (CTP-Os) of approximately one in every 20,000 cells. Utilizing this CFU assay, the unique property of many CTP populations (e.g. CTP-Os) to preferentially and rapidly adhere to selected surfaces has been investigated, particularly with regard to surfaces that can be created or utilized in a porous implantable matrix or scaffold. This investigation resulted in the recognition of the process of selective retention, which has been used to develop the Cellect™ graft preparation device, now manufactured and marketed by DePuy Spine Inc.

Selective Retention (SR) involves passing a cell suspension through a porous matrix and uses the intrinsic attachment behavior to retain CTP-Os in the matrix, while non-adherent cells pass through the matrix in the effluent solution. SR has been used to enrich CTP-Os as much as 16 fold. See Muschler et al., Clin. Orthop. Rel. Res. (2003) 407, p. 102-118. Current scaffolds used for SR (e.g., bone matrix, TCP ceramic) will retain 80-90% of CTP-Os and only 20-30% of other nucleated cells, resulting in a 3-4 fold increase in the CTP concentration and also a 2-3 fold increase in CTP prevalence by removing 70-80% of potentially competing cells. Thus, while effective, the principal limitation of selective retention is the fact that many of the vastly more abundant non-progenitor cells also bind to the same surfaces, and although they are less adherent, they occupy a much larger fraction of available surface. SR processing has the advantage of requiring relatively simple instrumentation and a minimum of reagents, but is far from being optimized. Even in retained "CTP enriched" populations, CTP-Os represent only a small fraction of the retained cells (mean±0.05%).

Accordingly, there remains a need for a more selective marker and/or additional separation techniques that can be used to purify or enrich adult stem cells from the animal tissues in which they are found.

SUMMARY OF THE INVENTION

One aspect of the invention provides a method for enriching adult stem cells that includes the steps of obtaining a population of cells including one or more adult stem cells from animal tissue; contacting the population of cells with a recognition ligand specific for an ECM component retained to the surfaces of adult stem cells in said population; and using a separation method to remove cells from said population that are not bound to the recognition ligand, thereby enriching adult stem cells that are bound to the recognition ligand via said retained ECM component.

In one embodiment of this aspect of the invention, the animal tissue is connective tissue. In additional embodiments, the separation method can include magnetic separation, selective retention using a porous matrix, and/or an affinity column method. In another embodiment, the retained ECM component is hyaluronan. For this embodiment, additional embodiments can provide that the recognition ligand is hyaluronan binding protein.

In further embodiments of this aspect of the invention, the adult stem cells can include connective tissue progenitor cells. In another embodiment, the method increases the prevalence of adult stem cells by at least about 2-fold. In a further embodiment, the method includes delivering the adult stem cells to a tissue in a subject that is in need of repair. In embodiments involving tissue repair, further embodiments may include adult stem cells that are enriched and delivered to the tissue in the subject intraoperatively, and/or the tissue being bone tissue.

In another aspect, the present invention provides a method for detecting adult stem cells in a cell population that includes the steps of contacting the cell population with a recognition ligand specific for an ECM material component that is retained to the surfaces of adult stem cells; and detecting adult stem cells in the cell population by identifying one or more cells having the recognition ligand associated therewith or bound thereto.

In one embodiment of this aspect of the invention, the recognition ligand is a labeled recognition ligand. In another embodiment, the labeled recognition ligand is a labeled antibody. In further embodiments, the adult stem cells are detected in vivo or ex vivo. In yet further embodiments, the adult stem cells are detected using an immunoassay or flow cytometry.

In other embodiments of the method for detecting adult stem cells, the adult stem cells are detected in connective tissue. In another embodiment, the adult stem cells are connective tissue progenitor cells. In other embodiments, the ECM component is hyaluronan, and/or the recognition ligand is a hyaluronan binding protein. In yet another embodiment, the one or more cells having the recognition ligand associated therewith or bound thereto are further characterized to determine if they have other properties of adult stem cells.

Another aspect of the present invention provides a method of identifying an ECM component marker associated with a particular cell type that includes the steps of obtaining a population of cells including one or more cells of the desired type from animal tissue; contacting the population of cells with a recognition ligand specific for a particular ECM component; enriching the cells that have the recognition ligand associated therewith or bound thereto; and determining if the enriched cells have the properties of the desired cell type.

In one embodiment of this aspect of the invention, the cells of the desired type are adult stem cells. In another embodiment, the adult stem cells include connective tissue progenitor cells. In yet another embodiment, the properties include proliferation that is different from that of non-adult stem cells.

Yet another aspect of the invention provides a method for enriching adult stem cells that includes the steps of obtaining a population of cells including one or more adult stem cells from animal tissue; contacting the population of cells with a recognition ligand specific for an EMC component or antigen that is present to a lesser degree on adult stem cells than on other cells in the population; and using a separation method to remove cells that are bound to a recognition ligand from the adult stem cells that are not bound to the recognition ligand.

In one embodiment of this aspect of the invention, the ECM component or antigen is absent from adult stem cells in the population. In other embodiments, the separation method can include magnetic separation, selective retention using a porous matrix, and/or affinity column methods. In another embodiment, the adult stem cells include connective tissue progenitor cells. In a further embodiment, the method enriches the prevalence of adult stem cells in said population by at least about 2-fold.

Unless otherwise specified, "a," "an," "the," and "at least one" are used interchangeably and mean one or more than one. Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 1 provides a schematic illustration of an adult stem cell that has been bound by a recognition ligand and has been further bound to a magnetic particle in preparation for separation by magnetic separation.

DETAILED DESCRIPTION OF EMBODIMENTS OF THE INVENTION

The invention described herein identifies a new method that can be used to select, concentrate, enrich, purify, deplete or fractionate populations of adult stem cells based upon using unique components of the extracellular matrix (ECM) retained on their surface as one or more discriminating markers. The invention is based in part on the discovery that different stem cell populations can be located in tissues within an environment or niche that is characterized by a specific relationship between the cell and its neighboring cells or extracellular matrix, and that this relationship and either cell-cell or cell-matrix interactions may be instrumental in maintaining the size and biological state and potential of local adult stem cells (tissue forming cells). The present invention thus provides a method for the rapid enrichment or purification of adult stem cells by targeting ECM material retained by those cells.

Accordingly, one aspect of the present invention provides a method for enriching or purifying adult stem cells. First, a population of cells including one or more adult stem cells is obtained from animal tissue. Next, the population of cells is contacted with a recognition ligand specific for ECM components retained by an adult stem cell. Once the recognition ligand has bound to the adult stem cells, a separation method is used to remove cells that are not bound to a recognition ligand from the adult stem cells bound to the recognition ligand.

Enrichment and/or purification, as used herein, involves increasing the prevalence of adult stem cells in a cell population as a result of selecting adult stem cells and/or depleting non-stem cells from a cell population, and does not require that the absolute number of adult stem cells in the population be increased. Furthermore, enrichment and/or purification, as used herein, refers to an increase in the prevalence of adult stem cells in a sample, but is not meant to imply that all other cells and/or other materials are excluded from the sample (i.e., a 100% purification). Rather, enrichment and/or purification represents various levels of an increased prevalence of adult stem cells, as further described herein.

Concentration, as used herein, refers to the number of cells in a given volume of sample. An increased concentration of adult stem cells in a cell population thus refers to a higher number of cells relative to the total volume. While the techniques used to enrich and/or purify the adult stem cells may result in a change in concentration, the concentration can be readily modified upwards or downwards by changing the volume of the sample.

Adult stem cells, as defined herein, are relatively undifferentiated cells found throughout the body after embryonic development that have the capacity to proliferate and generate progeny that are capable of differentiating to contribute to the formation of new tissues. This definition includes not only the most primitive undifferentiated cells in adult tissues, but also the progeny or "progenitor cells" resident in new tissue that are themselves derived from primitive stem cells but are capable of proliferation. While referred to herein as adult stem cells, it is to be understood that both stem cells and progenitor cells capable of generating progeny that contribute to new tissue formation can be obtained from subjects having a variety of ages, and not just adults. Adult stem cells and progenitor cells include cells derived from a variety of different tissues. For example, adult stem cells include connective tissue progenitor cells, adipose-derived adult stem cells, hematopoietic stem cells, mammary stem cells, mesenchymal stem cells, endothelial stem cells, neural stem cells, olfactory adult stem cells, and spermatogonial progenitor cells. Adult stem cells also include stem cells that have varying degrees of potential to differentiate into different tissues. For example, adult stem cells include pluripotent stem cells that can differentiate into cells derived from any of the three germ layers, multipotent stem cells that produce cells of a closely related family of cells (e.g., hematopoietic stem cells), and unipotent cells that can product only a single cell type but have the ability to self-renew.

The method for enriching or purifying adult stem cells includes obtaining a sample comprising a population of cells including one or more adult stem cells from animal tissue. The population of cells represents the initial collection of a variety of different types of cells found at a tissue site, of which only a small fraction are generally adult stem cells. However, in order for the population to be expected to include one or more adult stem cells, it is preferred that the population of cells obtained should have a size of 100 or more cells, depending on the local density of adult stem cells, with much higher populations (e.g. over one million cells) being preferred for a typical cell population.

The population of cells may be obtained by aspirating the animal tissue by various methods known to those skilled in the art. For example, a needle and syringe may be used to penetrate the tissue and then apply negative pressure to withdraw the desired cells. The amount of negative pressure applied should be sufficient to withdraw the desired cells from the surrounding tissue, and do so with sufficient force to obtain one or more adult stem cells that retain extracellular matrix material. The size of the needle will vary depending on the type of animal tissue involved. For example, when the population of cells is obtained from blood, a needle with a diameter from about 22 gauge to about 14 gauge may be used. For bone marrow, a large needle with a diameter from about 1 mm to about 6 mm may be used. For adipose tissue, an even larger need with a diameter from about 3 mm to about 12 mm may be used.

The populations of cells typically obtained from a sample of bone marrow aspirate includes nucleated progenitor cells, nucleated hematopoietic cells, endothelial cells, and cells derived from peripheral blood, including red cells and platelets. Note, however, that there are several other cell types present in an aspirate, including stromal cells, pericytes, and reticulocytes. Because a bone marrow aspirate contains peripheral blood, it is preferred that the aspirate be collected in a syringe containing an anticoagulant. Suitable anticoagulants include heparin, sodium citrate, and EDTA. Preferably, a bone marrow aspirate for use in a method of the present invention is obtained from the patient who will receive the graft (the graftee). Less preferably, the bone marrow aspirate can be obtained from another immunologically compatible donor.

The population of cells can be obtained from a variety of different animal tissues, depending on the type of adult stem cells being sought. Animal tissue, as used herein, is tissue obtained from animals including, for example, humans and domesticated animals such as farm animals and pets. Animal tissues include a variety of tissues such as epithelial tissue, connective tissues, muscle tissue, and nerve tissue. These categories include a variety of more specialized forms of tissue. For example, connective tissue includes blood vessels, lymphatic tissue, cartilage, bone, marrow stroma, tendon, and adipose tissue. Animal tissue may be obtained from the desired tissue site using a variety of methods known to those skilled in the art, such as biopsy or aspiration. Animal tissue may contain a variety of different types of adult stem cells. For example, bone marrow contains multiple subsets of adult stem cells that are capable of contributing to new tissue formation: hematopoietic (blood) progenitors, vascular progenitors, and bone, fat, muscle, fibrous tissues (tendon, ligament, scar), cartilage, and marrow stroma.

Adult stem cells within the heterogeneous population of cells can present a potentially discriminating array of ECM material retained to their surface, reflecting the unique niche where they are naturally present. These ECM materials may be retained to stem cell surfaces via physical interactions that do not exclude, or necessarily include, chemical bonding. In order to utilize this retained ECM material, the population of cells obtained from animal tissue is contacted with a recognition ligand specific for extracellular matrix (ECM) material that is retained, or that is retained to a greater degree relative to other cells, by an adult stem cell. In order to bring the recognition ligands into contact with the population of cells, the recognition ligands can be placed into the solution or a sample containing the population of cells. The recognition ligand specific for ECM retained by an adult stem cell selectively binds to the unique ECM components that have been retained on the adult stem cell. That is, in a given sample of animal tissue, it has been discovered that adult stem cells may tend to be concentrated in a relatively higher prevalence in specific regions of the extracellular matrix (ECM) for that tissue, as compared to the tissue and its ECM as a whole. It has also been discovered that certain components of the ECM also may be more highly concentrated in these areas where stem cell prevalence is high, compared to other components of the ECM for the entire tissue sample or tissue type. As a result, ECM components that are more highly concentrated in these specific regions have been found to be more likely retained, or retained to a greater degree, to the surfaces of adult stem cells that are derived from a sample of the tissue, than to other cells or cell types that make up the specific tissue type or sample.

As used herein, the phrase "selectively binds" and other permutations of that phrase refer to a recognition ligand (e.g., an antibody or binding protein) that will, under appropriate (e.g., physiological) conditions, interact with a cell surface or cell associated component (e.g., an antigen present on ECM material) preferentially or to a greater degree compared to a different or structurally unrelated cell surface component or cell associated component. Recognition ligands include antibodies and other types of proteins, peptides, carbohydrates, lipids, macromolecules, small organic molecules, and the like that selectively bind to the desired target (e.g., ECM retained by an adult stem cell).

As noted above, the inventors discovered that when cells from native tissue are isolated they may retain on their surface not only membrane bound molecules, which have been the focus of cell isolation and characterization procedures to date, but they may also retain on their surface molecules that are derived from the extracellular matrix niche that they occupied when in vivo. Stem cell populations are established in specific anatomic locations referred to as niches that save stem cells from depletion while protecting the host from excessive stem-cell proliferation. These niches provide a wide variety of inputs to the stem cells to control stem cell activity, such as paracrine signaling, humoral input, neural input, metabolic cues, cell to cell interactions, and extracellular matrix interactions. See Scadden, Nature (2006), Vol. 441, 29 June, p. 1075-1079. In particular with regard to the present invention, the unique extracellular matrix material present in adult stem cell niches may be retained by adult stem cell and used to aid in their detection and purification. For example, ECM molecules can be detected on the surface of the freshly isolated bone marrow-derived cells.

The extracellular matrix is the extracellular part of animal tissue that provides structural support and various other benefits to cells in animal tissue. As used herein, ECM retained by adult stem cells refers to ECM material or component(s) that are associated with the surface of the adult stem cells. In particular, the retained ECM is extracellular matrix material that remains associated with the adult stem cells when they have been removed from tissue by techniques such as aspiration, as described herein. The ECM material is retained in association with the adult stem cells by the same binding processes which serve to associate ECM material with cells in vivo, such as binding by integrin. For example, hyaluronan is retained on the surface of adult stem cells by a variety of hyaluronan binding proteins and receptors (e.g., CD44) referred to as hyaladherins. The mechanisms by which cells adhere to the ECM are well known to those skilled in the art. For further information regarding hyaladherins, see Day et al., J. Biol. Chem. (2002) February 15; 277(7), p. 4585-8.

The extracellular matrix includes proteoglycan matrix components and non-proteoglycan matrix components. Proteoglycan matrix components include, for example, heparin sulfate proteoglycans, chondroitin sulfate proteoglycans, and keratan sulfate proteoglycans. The non-proteoglycan matrix components include hyaluronan, collagen, fibronectin, laminin, vitronectin, and elastin. Some ECM components are relatively ubiquitous molecules that may not be useful for isolating the adult stem cells. However, some of the ECM components retained on the surface of newly obtained cells can be discriminating and valuable in selection of adult stem cells, or, in the alternative, depleting a population of non-stem cells. The ECM material that are useful to enrich or purify adult stem cells found in one type of tissue can be different from the ECM material useful for enriching or purify adult stem cells in another tissue. For example, while hyaluronan is useful for identifying adult stem cells present in bone marrow, other ECM material may be useful for identifying adult stem cells present in other tissues such as adipose tissue.

Preferably, the ECM component used for ligand targeting is retained on the surface of adult stem cells at much higher levels than compared to the other cell types in the tissue of interest. For example, it may be found at levels at least twice as high, and more preferably at levels at least five times as high on adult stem cells in comparison to non-adult stem cells. In further embodiments, the retained ECM component is exclusively retained on adult stem cells in a specific tissue type upon extraction or aspiration.

In one embodiment, the recognition ligand is an antibody that selectively binds a unique component of the ECM material that is selectively retained to the adult stem cells. For example, the antibody may selectively bind to hyaluronan. Hyaluronan (HA) is a large molecular weight polysaccharide molecule that is present in many adult tissues, particularly in the dermis, in the vitreous of the eye, and in articular cartilage. HA also makes of the zona pelucida around the human oocyte, through which the sperm must penetrate to come in contact with the egg. HA is a repeating linear polymer comprised of D-glucuronic acid and D-N-acetylglucosamine, linked together via alternating $\beta$-1,4 and $\beta$-1,3 glycosidic bonds.

Other than the three exceptions in adult tissues mentioned above (cartilage, dermis, and eye), HA is a relatively minor component of the extracellular matrix of most tissues. However, HA is markedly upregulated and a prominent feature in inflammation and the response of tissues to injury, and the regenerative environment that may follow these insults. The present inventors have demonstrated that HA is also relatively abundant in the perivascular space around small blood vessels in the marrow space, and is also present in the pericellular region around a small fraction of fibroblastic or stromal-like cells that are scattered with in the bone marrow space. See Midura et al., J. Biol. Chem. (2003) December 19; 278(51), p. 51462-8.

Based on these observations, the inventors hypothesized that hyaluronan may be an important extracellular-matrix component that may relate to the function of adult stem cells. Moreover, even if HA was not related to their function per se, it was at least hypothesized that HA is more heavily concentrated in niches where stem-cell prevalence is high, which might suggest a novel method to detect and isolate them. If HA concentration is relatively higher, compared to other ECM components, in stem cell niches, HA could be more likely to be retained, or to be retained in higher concentrations, by extracted cells. This, in turn, could be used to purify stem cells from other cell types.

Experiments to test these hypotheses and also test the hypothesis that cells that retain HA on their surface would either be more or less likely to exhibit colony forming activity (which is indicative of adult stem cells) were carried out. Briefly, biotinylated G1-link protein (a hyaluronan binding protein) was used to label cells containing HA on their surface soon after isolation and to link these cells with magnetic beads to enable separation in a magnetic field. Further details are provided in Example 1 herein. These experiments demonstrated not only that bone marrow derived cells can be rapidly separated into separate cell populations that do and do not present HA retained on their surface, but more importantly that cells that present HA on their surface are significantly enriched with respect to the prevalence of colony forming units that express an osteoblastic phenotype under osteogenic conditions in vitro, both of which indicate that the enriched cells are adult stem cells.

In some embodiments, the recognition ligand is an antibody. The term antibodies, as used herein, includes vertebrate antibodies, hybrid antibodies, chimeric antibodies, humanized antibodies, altered antibodies, univalent antibodies, monoclonal and polyclonal antibodies, Fab proteins and single domain antibodies. Preferred types of antibodies used as recognition ligands for the present invention include monoclonal and polyclonal antibodies. These types of antibodies are generally prepared by differing procedures.

If polyclonal antibodies are desired, a selected animal (e.g., mouse, rabbit, goat, horse or bird, such as chicken) is immunized with the desired extracellular matrix material. Serum from the immunized animal is collected and treated according to known procedures. Serum containing polyclonal antibodies to an extracellular matrix material can be purified by using an affinity column method. Techniques for producing and processing polyclonal antisera are known in the art (see for example, Mayer and Walker eds. Immunochemical Methods in Cell and Molecular Biology (Academic Press, London) (1987), Coligan, et al., Unit 9, Current Protocols in Immunology, Wiley Interscience (1991), Green et al., Production of Polyclonal Antisera, in Immunochemical Protocols (Manson, ed.), pages 1-5 (Humana Press 1992); Coligan et al., Production of Polyclonal Antisera in. Rabbits, Rats, Mice and Hamsters, in Current Protocols in Immunology, section 2.4.1 (1992)).

Monoclonal antibodies directed against an extracellular matrix material are readily produced by one skilled in the art. The general methodology for making monoclonal antibodies by hybridomas is well known. Immortal antibody-producing cell lines can be created by cell fusion, and also by other techniques such as direct transformation of B lymphocyte cells with oncogenic DNA, or transfection with Epstein-Barr virus (See Monoclonal Antibody Production. Committee on Methods of Producing Monoclonal Antibodies, Institute for Laboratory Animal Research, National Research Council; The National Academies Press; (1999), Kohler & Milstein, Nature, 256:495 (1975); Coligan et al., sections 2.5.1-2.6.7; and Harlow et al., Antibodies: A Laboratory Manual, page 726 (Cold Spring Harbor Pub. 1988)). Panels of monoclonal antibodies produced against extracellular matrix material can be screened for various properties such as epitope affinity.

In other embodiments, the recognition ligand is something other than an antibody. For example, the recognition ligand can be a binding protein. More specifically, a hyaluronan binding protein can serve as a suitable non-antibody recognition ligand. There are a variety of proteins that can be referred to as hyaluronan binding proteins. For example, crosslinked G1-Link protein is a synthetic hyaluronan binding protein prepared from aggrecan components that binds to hyaluronan with high affinity.

After the population of cells has been contacted with a recognition ligand specific for ECM retained by an adult stem cell, a separation method is used to remove or diminish cells from the sample that are not bound to the recognition ligand, which will leave behind an enriched (i.e., more prevalent) population of the adult stem cells, which are bound to the recognition ligand. Removing cells that are not bound to a recognition ligand can have several effects on the population of cells. For example, it may represent a method of enriching the percentage of adult stem cells bound to a recognition ligand that are left after separation. It may also represent a method for increasing the percentage of adult stem cells bound to a recognition ligand from the entire, whole population of cells in the tissue-derived sample. In addition, it may also represent a method for enriching or purifying adult stem cells from a population of cells based on their binding to a suitable recognition ligand via the retained ECM component. Finally, for some applications, it can represent a method for depletion of an undesired population of cells, by focusing on the removed cells that are not bound to a recognition ligand.

Separation of cells bound to the recognition ligand from cells that are not bound to the recognition ligand can be carried out using a wide variety of techniques. Examples of separation methods that can be used include magnetic separation, fluorescence activated cell sorting (FACS), density separation, affinity column methods, or selective retention using a porous matrix. Multiple separation methods can also be combined to achieve higher levels of cell enrichment or purification. Embodiments of the invention may provide a 2-fold, a 4-fold, or a 10-fold enrichment of the population of adult stem cells. Additional embodiments may provide a 50-fold or a 100-fold enrichment of adult stem cells.

In one embodiment of the invention, the separation method includes the use of magnetic separation. Magnetic Separation (MS), which is sometimes referred to by the trade name MACS®, uses selective cell surface markers to magnetically label cells (e.g., microbeads) and separate the labeled and unlabeled cells in a magnetic field. Generally an antibody to a surface antigen is linked by a secondary antibody to a bead. A cell may be labeled with no beads or multiple beads, in proportion to antigen density, and is accelerated in the magnetic field in proportion to the number of bound beads. Clinical MS systems (e.g., Dynal MPC™ (Invitrogen), MACS™ columns (Milthenyi Biotec, Bergisch Gladbach), BD IMag™ (BD Biosciences) and EasySep™ (StemCell Technologies)) have been used to enrich CD34+ hematopoietic progenitors 10-100 fold. See Lang et al., Blood (2003) 101(4), p. 1630-6. Automation (e.g., CliniMACS) has allowed the use of MS separation in smaller clinical centers.

Two different strategies are currently available for use in MS; Capture-Release (CR) and Continuous Magnetophoresis (CM). CR generally involves placing a container with labeled cells into a magnet (e.g., EasySep™). Labeled cells are retained against the container wall while non-magnetic cells are removed. In continuous magnetophoresis (CM), on the other hand, labeled cells are passed through a laminar flow system where they are continuously separated by pulling them from an inner to an outer stream path. By eliminating the need for surface retention, CM is particularly well suited for high throughput processing, even using weakly magnetic, colloidal or molecular reagents (e.g., nano-beads). An isodynamic field is used, providing a constant radial force, but not a constant field. Sorting kinetics are predictable, based on magnetophoretic cell mobility, field and gradient, channel geometry, flow rate, and labeling reagents. For additional details, see Zborowski et al., Separation Science and Technology (2002) 37, p. 3611-33 and Moore et al., Anal. Chem. (2004) 76(14), p. 3899-907.

The isolation of adult stem cells including retained hyaluronan using magnetic beads has an additional desirable feature, in that a simple digestion step with *Streptomyces hyaluronidase*, an endo eliminase that is specific for hyaluronan, can be used to remove the magnetic bead/link protein complex, further reducing the possibility of an adverse reaction associated with the bead or an immune response to the bovine hyaluronate binding protein.

FIG. 1 provides a schematic illustration of an adult stem cell that has been bound by a recognition ligand via a surface-retained ECM component, and has been further bound to a magnetic particle in preparation for separation by magnetic separation. The FIGURE shows an adult stem cell 10 that is surrounded by retained ECM 12 (e.g., hyaluronan). A recognition ligand 14 is bound to the retained ECM 12. The recognition ligand 14 includes a binding antigen 16 (e.g., biotin) that can be recognized by double-sided antibody 18. The double-sided antibody 18 includes an antigen binding site 20 with affinity for the binding antigen 16, a particle binding site 22 with affinity for a magnetic nanobead 24, and a linker molecule 26 that connects two antibodies to provide the double-sided antibody 18. Note that while the FIGURE shows a double-sided antibody 18 that includes two typical antibodies, other binding proteins (e.g., streptavidin) can be used to replace one or both of the antibodies used in the double-sided antibody 18.

Separation of cells bound to the recognition ligand from cells that are not bound to the recognition ligand can also be carried out using affinity column method. To separate cells bound to the recognition ligand using affinity column method, the recognition ligand for ECM component can be bound to the a column material and a population of cells including adult stem cells retaining ECM material can be run through the column which provides a surface on which they will be preferentially retained by adherence to the recognition ligand. Typically the recognition ligand is covalently bound to the surface of the column material. Various types of column material can be used to provide the surface upon which the recognition ligand is provided within the affinity column (e.g. glass, sepharose or polymeric beads, fibers, or porous matrix). For example, if hyaluronan was being used as the target ECM material, a hyaluronan binding protein could be covalently bound to glass beads to provide a column matrix. After the population of cells has been placed in the affinity column, the column is washed, and then an elution buffer or other agent can be to the column in order to release the adult stem cells that have been retained by the affinity column. Again, using hyaluronan as an example, retained cells can be released using hyaluronidase (e.g. *Streptomyces hyaluronidas*) in the elution buffer in order to cleave the hyaluronan to elute the retained cells. It should be noted that the use of the term "affinity column method" does not imply the need for a traditional physically constrained cylindrical or vertical column. While traditional methods for "affinity column" separation often use a surface that is fixed and in which gravity flow past a fixed surface is used as the means of exposing cells to the surface, affinity methods are not limited to the use of a fixed physical column. The affinity surface can be non-fixed, suspended and moved through the cell suspension to accomplish retention and separation, for example in a manner comparable to the use of colloid, beads or resin chemical separation methods.

A variety of different configurations for separation by use of an affinity column are available. For example, as is well known to those skilled in the art, sandwich techniques in which antibodies are bound to the column that have an affinity for the recognition ligand itself can also be used, in which case the recognition ligand is bound to the adult stem cells before passing them through the column. An example of an affinity column using a sandwich technique would be an affinity column in which streptavidin coated glass beads were used to provide the matrix, and the population of cells was contacted with biotinylated hyaluronan binding protein before running it through the column. Affinity columns suitable for use with magnetically labeled particles are also available from suppliers such as Miltenyi Biotec Inc.

The separation method can also include multiple iterations of the separation process in which the cells bound by the recognition ligand are separated from the cells that are not bound by a recognition ligand. For example, the separation method can be carried out twice, three times, four times, or greater than four times in order to obtain the desired level of purification. In addition to encompassing the use of multiple iterations of the separation process, the separation method can include the use of multiple types of separation methods. For example, magnetic separation can be used together with affinity chromatography or selective retention using a porous matrix. ECM marker selection does not exclude or interfere with other methods of adult stem cell enrichment or purification, and can thus be readily combined with other method of cell selection or depletion in a multistep processing strategy, if desired.

Separation of cells bound to the recognition ligand from cells that are not bound to the recognition ligand can also be carried out by selective retention using a porous matrix. Selective retention is similar to affinity column methods in that porous matrix has an affinity for adult stem cells or for the recognition ligands bound to the adult stem cell via a retained ECM component. However, unlike an affinity column, the porous matrix of the select retention system is removed and delivered to supply adult stem cells, rather than removing the adult stem cells from the affinity column by elution before use. The porous matrix used in selective retention can be a bone matrix or similar material when selective retention is used to increase the concentration and/or enrich adult stem cells, and in this embodiment includes a combination of particulate and fibrous bone materials. Use of selective retention using a porous matrix to enrich a progenitor cell population is described in U.S. Pat. No. 6,723,131, issued to Muschler, the disclosure of which is incorporated herein by reference.

For use in the present invention, selective retention can be used alone, or to supplement cell separation by other techniques such as magnetic separation or affinity column methods. When combined with another purification technique, it is generally preferable to carry out selective retention as the final step, because the adult stem cells are retained in the porous matrix. When used alone, selective retention in the present invention should be modified to include use of a retention-ligand specific for ECM material retained by adult stem cells. The retention-ligand is attached to the porous matrix used in the selective retention system in order to increase the retention of adult stem cells by the porous matrix. For example, a hyaluronan-binding protein can be attached to the porous matrix of a selective retention system in order to increase the purification of adult stem cells that include retained hyaluronan.

An additional method that may be used to supplement the enrichment or purification of the adult stem cells is negative selection. When using negative selection, the process of using a recognition ligand specific for ECM retained by adult stem cells is reversed, and a recognition ligand is used that is selective for non-stem cells. Accordingly, in supplemental purification using negative selection, the population of cells is mixed with a recognition ligand that binds to non-adult stem cells through either retained ECM or cell surface components, and the bound cells are then removed, leaving a cell population that is enriched for adult stem cells. Negative selection can be carried out using any of the described separation techniques, such as affinity column methods or magnetic separation. Examples of antigens suitable for use as targets for negative selection recognition ligands include antigens that are found on differentiated non-stem cells, but not on stem cells, such as CD45, CD34, and GLY-A.

Embodiments of the method of enriching or purifying adult stem cells of the invention can requires less than sixty minutes to complete. Rapid intra-operative processing of tissues for progenitor banking programs can involve either autogenous cell banking or allograft cell banking strategies. Thus, the adult stem cell purification can be performed while the source of the cell population (e.g., the patient) is in the operating room, and the cells rapidly delivered back to the patient. Accordingly, the number of occasions the patient must undergo invasive procedures to receive an infusion of adult stem cells can be reduced using the present methods. Rapid processing of tissue-derived adult stem cells using retained ECM surface markers is expected to reduce cost, time and risk associated with alternative strategies involving in vitro culture expansion of progenitor cell populations. Examples of purification techniques suitable for rapid intra-operative processing include a selective retention system including a recognition ligand specific for ECM material retained by an adult stem cell or an affinity column that includes a recognition ligand already bound to the beads of the matrix, or a readily used sandwich system (e.g., hyaluronan binding protein together with magnetic particles).

The present invention also provides a method for detecting adult stem cells in a cell population that includes contacting the cell population with a recognition ligand specific for ECM material retained by an adult stem cell and detecting the adult stem cells in the cell population by identifying sample cells bound by the recognition ligand. The adult stem cells detected can be any of the types of adult stem cells described herein, such as connective tissue progenitor cells. Detection of adult stem cells using clinical assays can be used, for example, for research or to characterize the health of patients through biopsy and analysis of the adult stem cell population present in tissues. Knowledge of adult stem cells levels can be useful for evaluating tissue regrowth or identifying adult stem cells and/or adult stem cell niches involved in cancer or in other disease processes.

The recognition ligand used to detect adult stem cells can be any of the recognition ligands described herein for use in enriching or purifying adult stem cells. For example, the recognition ligand can be an antibody or a binding protein such as a hyaluronan binding protein.

The recognition ligand used is specific for extracellular matrix (ECM) material retained by adult stem cells. The ECM retained by adult stem cells is ECM material that is associated with the surface of the adult stem cells, and includes proteoglycan matrix components and non-proteoglycan matrix components, as described herein. For example, the method may use recognition ligands that specifically bind to the ECM material hyaluronan.

The recognition ligand specific for ECM material can be either a labeled or un-labeled recognition ligand, depending on the nature of the method of detection being used. For example, if the recognition ligand is used alone (i.e., without use of other types of recognition ligands) the recognition ligand will generally include a label in order to detect material that has been bound by the recognition ligand. As already described herein, the label should be a compound that facilitates detection of the recognition ligand, such as an enzyme (e.g., peroxidase), a radioisotope (e.g., I-125), or a fluorescent compound (e.g., fluorescein). Attachment of labels to recognition ligands can be readily carried out using techniques well known to those skilled in the art.

The method of detecting adult stem cells in a cell population can be used to detect adult stem cells with retained ECM material in vivo. In order to bring the recognition ligands into contact with the population of cells, the recognition ligands can be administered to the tissue region that includes the cell population being studied. The recognition ligand conjugate can be administered to the subject by local administration; e.g., by injection into or near the tissue of interest, such as bone marrow tissue. The recognition ligand will then bind to adult stem cells having the corresponding ECM component retained and nearby cells in their niche, and can be detected by detecting the associated label, such as a radioisotope label. The adult stem cells can be detected in a variety of different tissues, such as epithelial tissue, connective tissues (e.g., bone marrow), muscle tissue, and nerve tissue.

Alternately, the method of detecting adult stem cells in a cell population with retained ECM material may be used ex vivo. Contacting the population of cells in an ex vivo sample is relatively simple in comparison with in vivo delivery, and can be done in the same fashion as described herein for purification of adult stem cells. Once the population of cells has been contacted, the cells that have been bound by the recognition ligand can be detected. If labeled recognition ligands are used, the cells can be detected directly. However, if un-labeled recognition ligands are used, the cells can be detected indirectly though a sandwich-type assay in which a labeled recognition ligand specific for the ECM-binding recognition ligand is also used.

For example, one method of detecting adult stem cells ex vivo is the use of flow cytometry. Flow cytometry is a precise and versatile means of cell identification in which cells in a focused stream of water flow past a laser beam and one or more fluorescent detectors so that individual cells are evaluated for various morphological traits, such as bearing a labeled recognition ligand. For example, adult stem cells in a cell population can be identified by flow cytometry by contacting the cell population with a recognition ligand specific for ECM material retained by an adult stem cell and then running the cells through a flow cytometer in order to detecting the adult stem cells in the cell population by identifying cells that have been bound by the recognition ligand. The recognition ligand can be readily detected by using a recognition ligand that bears a fluorescent label.

One variant of flow cytometry is fluorescence-activated cell sorting (FACS), which can be used to separate cells of interest in addition to identifying them. For example, cells labeled with recognition ligands specific for CD34, c-kit, and CD150 have been applied with some success to accomplish 100-1000 fold enrichment of hematopoietic stem cells by FACS. See for example Jankowski et al., Hum. Gene Ther. (2001) 12(6), p. 619-28. In addition to use in detecting adult stem cells, FACS can be used to enrich or purify stem cells in a manner similar to that described above for MACS®. However, FACS is limited by cost, issues of sterility, burden of reagents, and particularly by throughput limitations (about 25,000 cells/hr), and thus is less preferred than MACS® for actual cell purification.

Another method of detecting adult stem cells ex vivo is the use of an immunoassay. Immunoassays are well known by those skilled in the art, and can use either labeled recognition ligands or recognition ligands without label. Those using labeled reagents can be further divided into homogenous immunoassays and heterogeneous immunoassays, the latter of which involves a separation step. Heterogeneous immunoassays can further be competitive, in which ECM material competes with labeled ECM to bind with antibodies followed by measurement of the amount of labeled antigen bound to the antibody site, and noncompetitive "sandwich" immunoassays, in which adult stem cells with retained ECM are bound to an antibody site and then labeled antibody is bound to the retained ECM, after which the amount of labeled antibody on the site is measured. Any suitable immunoassay technique can be used to detect adult stem cells using recognition ligands specific for retained ECM material.

For example, adult stem cells in a cell population can be identified by immunoassay by contacting the cell population with a recognition ligand specific for ECM material retained by an adult stem cell in an assay kit and then providing a labeled recognition ligand specific for ECM material in order to detecting the amount of adult stem cells captured by the recognition ligand specific for ECM material (i.e., use of a noncompetitive immunoassay).

The method of detecting adult stem cells can also include additional steps to confirm that the cells bound by the recognition ligand are stem cells. For example, the one or more cells bound by the recognition ligand are further characterized to determine if they have the characteristics of adult stem cells. This can involve determining whether the cells can proliferate or differentiate as stem cells, or other features associated with stem cells such as cell size or morphology. In addition, in some embodiments, one or more additional recognition ligands specific for stem cells may be used to further characterize the cells being detected by the method.

The invention also provides a method for tissue repair using adult stem cells. The method includes the steps of enriching or purifying adult stem cells obtained from a subject, as described herein, and then delivering the adult stem cells to a tissue in the subject that is in need of repair. The invention thus provides a method for cell-based therapy using enriched or purified adult stem cells. Adult stem cells purified by the method described herein can be used to treat a variety of conditions in which tissue needs repair, such as Parkinson's and Alzheimer's diseases, spinal cord injury, stroke, wounds such as burns, heart disease, diabetes, osteoarthritis, and rheumatoid arthritis. For example, adult stem cells derived from bone marrow can be transplanted into a damaged heart where they generate heart muscle cells and successfully repopulate the heart tissue with differentiated myocardial cells.

The adult stem cells used to provide tissue repair can be connective tissue progenitor cells. Connective tissue progenitor cells can be used to treat a variety of types of tissue injury in connective tissues, such as the repair of bone, cartilage, tendons, or ligaments. Connective tissue progenitor cells can also for healing skin wounds, such as skin wounds caused by burns.

Tissue repair using adult stem cells can be carried out using a variety of different methods, kits, or devices. For example, adult stem cells purified or enriched by the invention can be injected locally into a tissue in need of repair, where the stem cells will repair the injured tissue. Alternately, the adult stem cells can be provided in a cell matrix such as that used in the Cellect™ system. In the Cellect™ system, bone material is used to provide a porous matrix in which connective tissue progenitor cells are concentrated and/or enriched. The porous matrix is then delivered to bone, where it provides an enriched source of stem cells. Similar matrices formed of appropriate tissue can be provided for other sites, thus allowing adult stem cells to be delivered to repair these tissues in a suitable biocompatible matrix. Alternately, rather than providing the adult stem cells in a cell matrix, the adult stem cells can be provided in a scaffold, which is a cell matrix that has been configured to provide a substrate to encourage the regrowth of a particular organ or tissue feature such as an ear.

The method of repairing tissue using adult stem cells enriched or purified according to the present invention can also use adult stem cells that are enriched or purified and delivered intraoperatively. In this type of method, a population of cells that includes adult stem cells is obtained from the subject and the adult stem cells are then purified and returned to the subject within a single treatment session (e.g. one procedure in and operating room (OR)). Preferably, the purification and return of the adult stem cells to a tissue in need of repair is carried out in 60 minutes or less. Methods suited to rapid purification of adult stem cells are described herein. For example, adult stem cells obtained by aspiration can be run through an affinity column method that already includes a recognition ligand bound to the matrix that is specific for ECM material retained by adult stem cells, washed and then eluted, and then delivered by injection to a tissue site in need of repair.

The invention also provides a method of identifying an ECM marker associated with adult stem cells. Adult stem cells found in various different tissues can have a variety of different ECM material associated with them, depending on the nature of the niche regions used to contain the adult stem cells in the particular tissue region. ECM markers associated with adult stem cells identified by this method can be used to isolate or detect adult stem cells as described herein. The method of identifying an associated ECM marker includes obtaining a population of cells that includes one or more adult stem cells from animal tissue, contacting this population of cells with a recognition ligand specific for ECM; enriching or purifying the cells bound to the recognition ligand; and then determining if the purified cells have the characteristics of adult stem cells. The method can be used, for example, to identify ECM markers associated with connective tissue progenitor cells.

The population of cells represents the initial collection of a variety of different types of cells found at a tissue site, of which only a small fraction are generally adult stem cells. The population of cells can be obtained by aspirating a tissue site, or by using other methods known to those skilled in the art. The population of cells can be suspended in a suitable buffer system to maintain the cells after they have been obtained.

The population of cells is then contacted with a recognition ligand specific for particular extracellular matrix components known or believed to be retained to or associated with the desired cell types to a greater degree than other cell types in the tissue of interest. Recognition ligands include antibodies and other types of proteins, peptides, small organic molecules, and the like that selectively bind to the desired target (e.g., ECM component retained by an adult stem cell). For example, the inventors have used hyaluronan binding protein as a recognition ligand that specifically binds to hyaluronan to determine that hyaluronan is associated with connective tissue progenitor cells. However, ECM includes a wide variety of antigens that can be used as a target for recognition ligands. Numerous ECM-associated antigens are known to those skilled in the art, and further antigens can be readily identified using antibodies and inhibition assays, followed by purification and characterization of the antigen. See, for example, Varki et al., eds., Essentials of Glycobiology, 1$^{st}$ edition, (2002). Accordingly, the techniques disclosed herein can be used to isolate, enrich the prevalence of other cell types within a heterogeneous population of cells from various tissues once particular ECM components that are more prevalently retained to or associated with the desired cell type have been identified. Methods for identifying particular ECM components that may be more prevalently retained to or associated with other cell types besides adult stem cells are described immediately above.

The cells bound to the recognition ligand are then enriched or purified, as described herein. For example, cells may be enriched or purified by magnetic separation or affinity column method. The enriched or purified cells are then characterized to determine if they are adult stem cells or any other cell type of interest. This is typically accomplished by determining if they have the characteristics of adult stem cells or other cells of interest (e.g. size, morphology, surface markers, gene expression profile, proliferative capacity, differentiation behavior). Stem cells can also be identified as stem cells with the capacity to proliferate to produce progeny that then differentiate and contribute to new tissue formation in response to appropriate environment or stimuli. Finally, if the enriched or purified cells have shown that they have characteristics that identify them as adult stem cells, then the ECM material that was used as a target antigen is thereby identified as being associated with that type of adult stem cell.

An embodiment of aspects of the present invention is illustrated by the following example. It is to be understood that the particular example, materials, amounts, and procedures are not limiting of the scope of the invention and are provided only in way of example.

Example 1

Positive Selection of Connective Tissue Progenitors Using Hyaluronan

A study was conducted to evaluate the use of surface-bound hyaluronan (HA) as a target for positive selection of connective tissue progenitors (CTPs) from a fresh bone marrow aspirate. Bone marrow was aspirated from 5 patients from the iliac crest in 2 mL aliquots according to approved IRB protocol. Two sequential buffy coats were performed to remove the bulk of the red blood cells, and bone marrow mononuclear cells (BMMNCs) were resuspended in buffer (PBS with 2% FBS and 1 mM EDTA).

Cells were processed through the EasySep™ Magnetic Separation system (Stem Cell Technologies Catalog #18543) on the basis of HA expression using a biotinylated G1 link protein (Sigma #H9910). Cells were resuspended in the recommended buffer (PBS with 2% FBS and 1 mM EDTA) at 100 million cells per milliliter in accordance with the manufacturer's protocols. Cells were stained with 200 microliters (µL) of an Fc blocker to prevent nonspecific uptake of antibodies, followed by 20 µL of biotinylated G1 link protein (hyaluronic acid binding protein, or HABP) at 0.5 mg/mL for one hour at room temperature. After removing excess HABP through a washing step, the EasySep anti-biotin tetrameric antibody complex was added at 200 µL per mL solution and allowed to incubate for 20 minutes at room temperature. The magnetic nanobeads were subsequently added at 100 µL per milliliter solution for 10 minutes. After increasing the total volume to 2.5 mL with the PBS buffer, the cells were put in the EasySep™ magnet for 5 minutes, and the unbound population was decanted. Cells retained in the magnet for 3 sequential separations were labeled as the purified $HA^{+++}$ population. Cells that were not retained were sent back through the magnet for a second pass. Any cells retained on the second pass were designated $HA^+$, since the magnetic labeling of these cells was not strong enough to retain them during the first round. Cells that were unbound on both passes through the magnet were considered $HA^-$. Samples from each of these three fractions were stained with trypan blue for viability, placed in 0.3% acetic acid to lyse RBCs, and counted with a haemocytometer.

$HA^{+++}$, $HA^+$ and $HA^-$ fractions, as well as unselected marrow, were cultured in osteogenic media consisting of alpha-MEM with bicarbonate and 10% FBS, 1% Pen/Strep, $10^{-8}$ dexamethasone, and 1% ascorbate. Each fraction was plated at a density of 1 million cells per LabTek slide, cultured at 37° C. at 5% $CO_2$ with media changes on Days 2 and 3. Day 6 cultures were fixed with 1:1 Acetone Methanol and stained for their nuclei with DAPI and for oseoblastic activity with Alkaline Phosphatase (AP).

Culture wells (4.2 cm$^2$) were scanned using a Spot RTSE 9.0 Monochrome-6 12 bit digital camera (Diagnostic Instruments Inc.) mounted on a Leica DMRBE motorized microscope controlled by Metamorph (v6.3) imaging software. 540 individual images of the culture well were aquired. A blank image was taken and used to background correct each individual image. The individual images were then montaged to create a single image of the entire culture well. A region of interest was defined to eliminate cell debris around the edges of the LabTek gasket. Cell nuclei segmentation was done using a global threshold and area calculation. Lint and apoptotic debris, as well as glass aberrations, were removed during this step.

Using a Euclidian distance map, cell nuclei were clustered into colonies containing eight or more cells where each nucleus was under 142.2 µm to its nearest neighbor. Each individual colony was quantified; providing a cell count, colony area (mm$^2$), colony density (cells/colony area), AP expression (AP area/cell number) and other morphologic information at a colony-by-colony level. In the pre-specified cases of debris detection, skipped colonies, and incomplete colony detection, the algorithm colony assessment was edited using the Colonize™ software system.

The observed prevalence of osteogenic CTPs (CTPs-Os) per million nucleated cells ($obsP_{CTP-O}$) under each condition was calculated based on the relationship $obsP_{CTP-O}$=CTP-O colonies observed/nucleated cells plated (in millions). For each colony the number of cells within the colony (nuclei count), colony area (mm$^2$) and cell density (cells per colony area) were determined. For each patient, the median value of all colonies for each colony level metric (cells, area and density) was calculated. The standardization of colony metrics was done to ascertain the effect of the treatment on the median colony outcome parameter and remove the effect of the known wide variation in CTP prevalence and performance between individual subjects.

Colony prevalence, median number of cells per colony, median colony area, median colony density, and median area fraction of alkaline phosphatase expression were summarized as follows. The distribution of each outcome was right skewed and Normal-theory analyses were conducted using a log base 2 transform. 95% confidence intervals on the log base 2 means were determined. A back transformation of the means and confidence intervals provided the geometric mean and the 95% confidence interval for the geometric means.

After magnetic separation, cell counts on each fraction ($HA^{+++}$, $HA^+$, and $HA^-$) were performed. On average, 3.3±1.2% of the total cells were retained in the $HA^{+++}$ population, 9.9±4.1% were found in the $HA^+$ population, and 86.7±4.5% were $HA^-$. Within these fractions, the $HA^{+++}$ cells were significantly enriched in CTPs, which an arithmetic average of 3.9-fold enrichment over the unselected marrow, and a 27.2-fold enrichment over the $HA^-$ fraction. The $HA^+$ and $HA^-$ fractions were significantly depleted in progenitors. The average prevalence of the unselected marrow control was 56 CTPs per million cells plated. The $HA^{+++}$ fraction was 168 CTPs per million cells plated, while the $HA^+$ and $HA^-$ fractions were 43 CTPs per million cells plated and 25 CTPs per million cells plated, respectively.

Proliferation was measured by the number of cells per colony. The $HA^{+++}$ population showed a significant increase in proliferation (2.1-fold increase), while the $HA^-$ fraction is significantly less proliferative (1.5-fold decrease) than the unselected marrow. $HA^+$ colonies show proliferative capabilities similar to the unselected marrow. Migration, measured by the cell density (number of cells/colony area), stayed fairly consistent across the unselected marrow, $HA^{+++}$, $HA^+$, and $HA^-$ fractions. Alkaline phosphatase (AP) activity was examined to gauge the differentiation of the CTPs. The $HA^+$ fraction showed significantly more differentiation (1.5-fold increase in AP expression), while the $HA^-$ fraction was significantly less differentiated (2-fold decrease) than the unselected marrow. While the HA$^{+++}$ fraction was also more differentiated (1.4-fold increase), this result was not statistically significant.

CTP "accounting" was also performed to access the total partitioning of CTPs after magnetic separation. The unselected marrow control predicted an average prevalence of 56 CTPs per million nucleated cells plated. Based on this prevalence, a prediction can be made of the total number of CTPs present in the starting population before processing through magnetic separation. After magnetic separation, the cell count for each fraction, multiplied by that fraction's prevalence, gives the total number of CTPs captured in the HA$^{+++}$, HA$^+$, and HA$^-$ populations, and also gives a measure of the CTP recovery after processing. For example, the HA$^{+++}$ fraction had an average prevalence of 169 CTPs/10$^6$ cells plated, and a mean of 3.3% of the staring population of cells were retained in the HA$^{+++}$ fraction. Calculating the number of CTPs partitioned to this fraction and dividing by the total number of predicted CTPs gives the percent of total CTPs found in this HA$^{+++}$ population. Averaging over the five patients, the results indicated a total CTP population capture of 14.3% in the HA$^{+++}$ fraction. The HA$^+$ fraction contained an additional 5.5% of the total CTPs, while the HA$^-$ fraction captured 36.0%. A number of the CTPs are unaccounted for after processing (44%), even though the majority of BMMNCs are present and viable (per trypan blue viability testing). This suggests that some CTPs are being lost during processing and separation, possibly due to their propensity to adhere to plastic surfaces.

The CTP population is enriched when selected for hyaluronan positive cells by magnetic separation. In comparison to colonies formed by CTPs from unselected marrow, progeny formed by HA$^{+++}$ CTPs are significantly more proliferative, although no significant difference was seen in migration or differentiation. With regards to the HA$-$ population, the HA$^{+++}$ fraction was enriched an average of 27.2-fold. However, it is clear that the HA$^{+++}$ fraction selects a subset of all CTPs, and that the HA$-$ population still contains a majority of CTPs (as well as the majority of all other bone marrow mononuclear cells). These highly proliferative HA$^{+++}$ cells may still offer superior performance in an in vivo graft environment, due to the elimination of the majority of non-essential, non-osteogenic cells that compete with CTPs for the limited oxygen and nutrients available at the graft site. This overwhelming disparity in metabolic demand limits the depth at which CTPs can remain viable in the graft, and these competing, non-osteogenic cells contribute to persistent inflammation as pro-inflammatory cytokines and cell debris are released after cell death. On average, 44% of CTPs are lost during the staining and magnetic separation process. It is unclear if some of the cells lose viability or the ability to attach to the culture slides after magnetization, but, given the robust colony formation of the adherent CTPs, this is doubtful. More likely, the inherent preference of CTPs to adhere to surfaces is the cause, as the staining and magnetization procedure provides ample opportunities for the CTPs to attach to the various equipment to which they are exposed. Steps to minimize the opportunity for CTPs to adhere include using low-retention pipette tips and streamlining the protocol by reducing the number of steps necessary as well as reducing the time required to process cells.

The complete disclosures of all patents, patent applications, and publications, and electronically available material cited herein are incorporated by reference. Any inconsistency between the material incorporated by reference and the material set for in the specification as originally filed shall be resolved in favor of the specification as originally filed. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method for enriching connective tissue progenitor cells comprising:
   obtaining a population of cells including one or more connective tissue progenitor cells isolated from animal adult connective tissue;
   contacting the population of cells with a hyaluronan binding protein which specifically binds surface-bound hyaluronan (HA) on connective tissue progenitor cells, wherein said hyaluronan is an extracellular-matrix component retained to the surfaces of said connective tissue progenitors cells from the extracellular-matrix niche region in which the connective tissue progenitor cells reside, and
   separating from said population of cells on the basis of HA retained to their surfaces, cells bound to hyaluronan from cells that are not bound to hyaluronan, wherein the separating increases a prevalence of the connective tissue progenitor cells by at least 2-fold, thereby enriching the connective tissue progenitor cells via hyaluronan retained extracellular-matrix component.

2. The method of claim 1, wherein the separation method comprises magnetic separation.

3. The method of claim 2, wherein the separation method further comprises selective retention using a porous matrix.

4. The method of claim 1, wherein the method further includes delivering the connective tissue progenitor cells to a tissue in a subject that is in need of repair.

5. The method of claim 4, wherein the connective tissue progenitor cells are enriched and delivered to said tissue in the subject intraoperatively.

6. The method of claim 4, wherein the tissue is bone tissue.

* * * * *

UNITED STATES PATENT AND TRADEMARK OFFICE
CERTIFICATE OF CORRECTION

PATENT NO. : 9,045,735 B2
APPLICATION NO. : 12/594493
DATED : June 2, 2015
INVENTOR(S) : George Muschler et al.

It is certified that error appears in the above-identified patent and that said Letters Patent is hereby corrected as shown below:

In the Specification

Delete the sentence spanning Column 1, Lines 14-17 under the heading STATEMENT OF GOVERNMENT-SPONSORED RESEARCH, and insert therefor the following substitute sentence:
--This invention was made with government support under AR042997 awarded by the National Institutes of Health. The government has certain rights in the invention.--

Signed and Sealed this
First Day of July, 2025

Coke Morgan Stewart
*Acting Director of the United States Patent and Trademark Office*